(12) United States Patent
Chao

(10) Patent No.: US 6,854,861 B2
(45) Date of Patent: Feb. 15, 2005

(54) TELESCOPIC UNIVERSAL FLASHLIGHT

(76) Inventor: Miao Li Chao, 235 Chung-Ho Box 8-24, Taipei (TW)

( * ) Notice: Subject to any disclaimer, the term of this patent is extended or adjusted under 35 U.S.C. 154(b) by 0 days.

(21) Appl. No.: 10/300,377

(22) Filed: Nov. 21, 2002

(65) Prior Publication Data

US 2004/0100795 A1 May 27, 2004

(51) Int. Cl.$^7$ ................................................. F21L 4/00
(52) U.S. Cl. .................. 362/197; 362/171; 362/178; 362/202; 362/188; 362/120; 362/204
(58) Field of Search ................................ 362/197, 198, 362/171, 178, 189, 195, 203, 204, 205, 200, 202, 188, 120

(56) References Cited

U.S. PATENT DOCUMENTS 5,975,712 A * 11/1999 Shiao ........................ 362/120
6,626,556 B2 * 9/2003 Galli ......................... 362/205
2003/0210543 A1 * 11/2003 Sharrah et al. ............. 362/187

* cited by examiner

Primary Examiner—Sandra O'Shea
Assistant Examiner—Bertrand Zeade

(57) ABSTRACT

A pleated bellows universal flashlight comprises a handle, a post and an illuminator. A battery and a power switch is installed in the handle; an upper side of the handle is extended with the post. An interior of the post is received with a conductive wire; the conductive wire has a section for extending a length of the conductive wire. A middle section of the post is installed with a pleated bellows portion which is both a telescopic and bendable snake-like tube. A connecting end of the post is installed with a retaining seat. One end of the retaining seat is connected to the conductive wire and another end thereof is connected to and fixes light emitting elements.

2 Claims, 4 Drawing Sheets

TELESCOPIC UNIVERSAL FLASHLIGHT

FIELD OF THE INVENTION

The present invention relates to joint, and particularly to a pleated bellows universal flashlight which is adjustable in length and orientation and can be connected to an illuminator for illumination

BACKGROUND OF THE INVENTION

In general, flashlights have a rigid structure, which are not adjustable in length and orientation so that it is often that the flashlight is inconvenient for lighting a deep or bending section, especially, in repairing some machines with large sizes and complicated structures. Moreover, a medical treatment, such as treating the diseases with ears, throats, etc., it is necessary to insert a flashlight into the deep portion of the organ. However, the prior art flashlight is not practical in theses applications.

SUMMARY OF THE INVENTION

Accordingly, the primary object of the present invention is to provide a pleated bellows universal flashlight, wherein the light source can be inserted into a deep dark place for illumination.

Another object of the present invention is to provide a pleated bellows universal flashlight which is light and portable.

To achieve above object, the present invention provides a pleated bellows universal flashlight which comprises a handle, a post and an illuminator. A battery and a power switch is installed in the handle. An upper side of the handle is extended with the post. An interior of the post is received with a conductive wire. The conductive wire has a section for extending a length of the conductive wire. A middle section of the post is installed with a pleated bellows portion which is both a telescopic and bendable snake-like tube. A connecting end of the post is installed with a retaining seat. One end of the retaining seat is connected to the conductive wire and another end thereof is connected to and fixes light emitting elements.

The various objects and advantages of the present invention will be more readily understood from the following detailed description when read in conjunction with the appended drawing.

DETAILED DESCRIPTION OF THE PREFERRED EMBODIMENTS

As shown in the figures, the pleated bellows universal flashlight of the present invention is illustrated. The pleated bellows universal flashlight comprises a handle 1, a post 2 and an illuminator, such as a bulb 32, etc.

The handle 1 is a post-like body. A battery and a power switch are installed therein. An upper side of the handle 1 is extended with the post 2. An interior of the post 2 is received with a conductive wire 11. The conductive wire 11 is left with a section for extending the length thereof. A middle section of the post 2 is installed with a pleated bellows portion which is both a telescopic and bendable snake-like tube.

Figure 1:
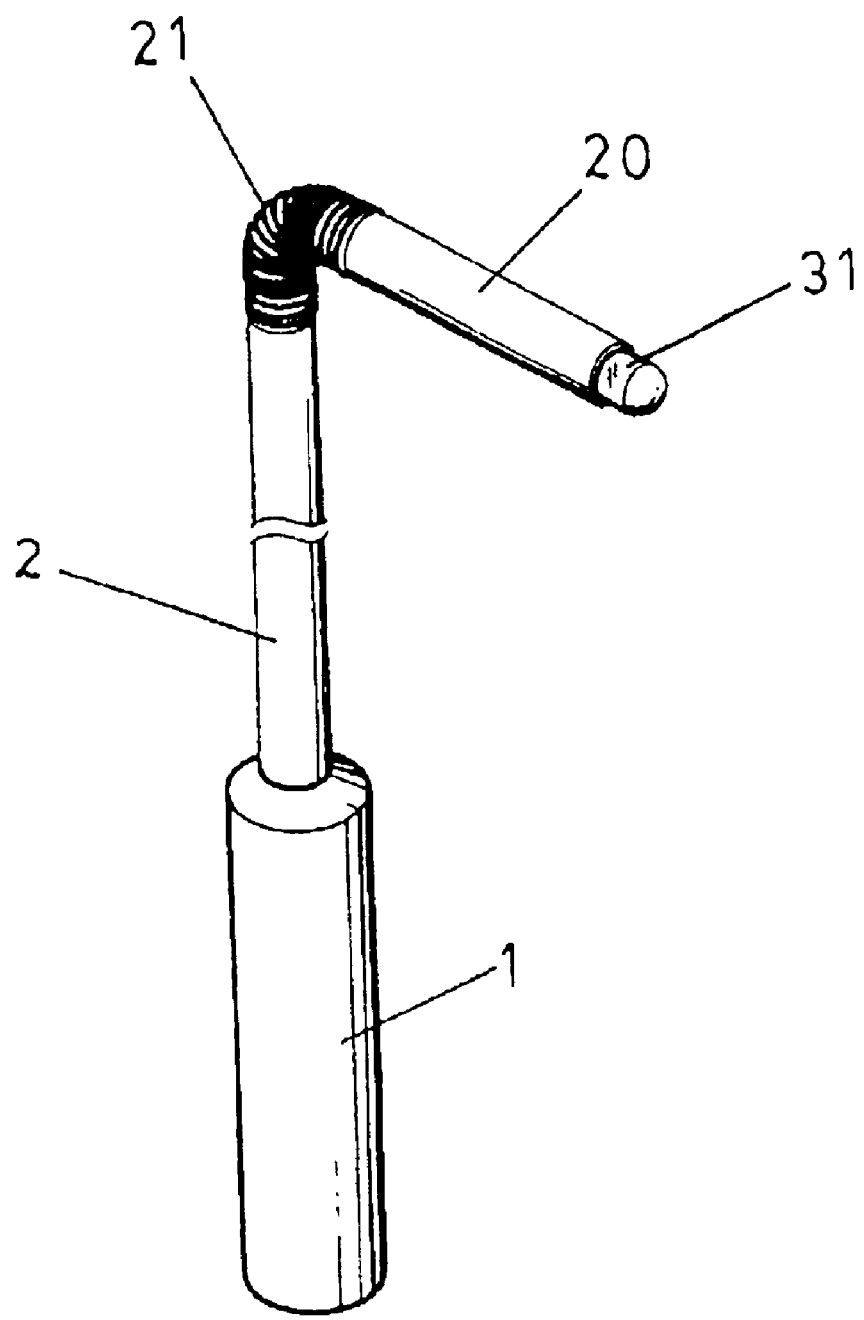
FIG. 1 is a structural view of the present invention.
Figure 2:
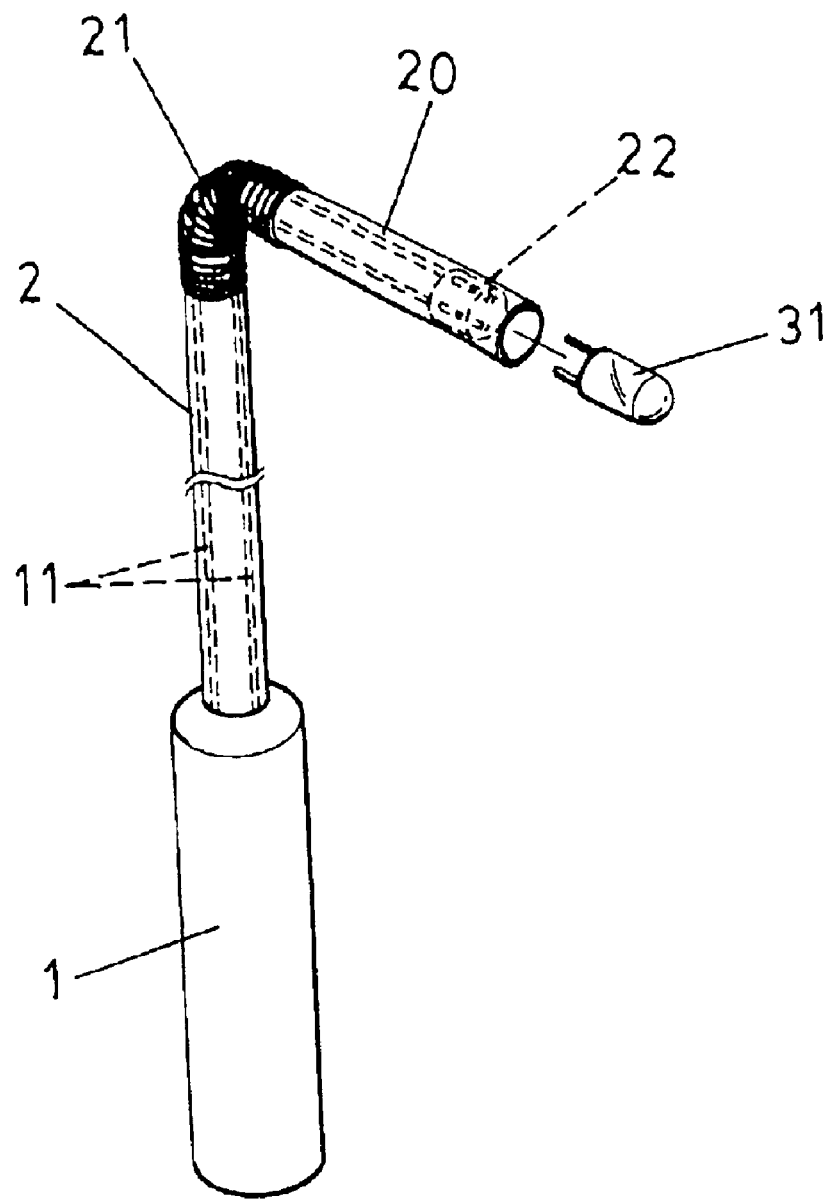
FIG. 2 is a schematic view showing the application of the present invention.
Figure 3:
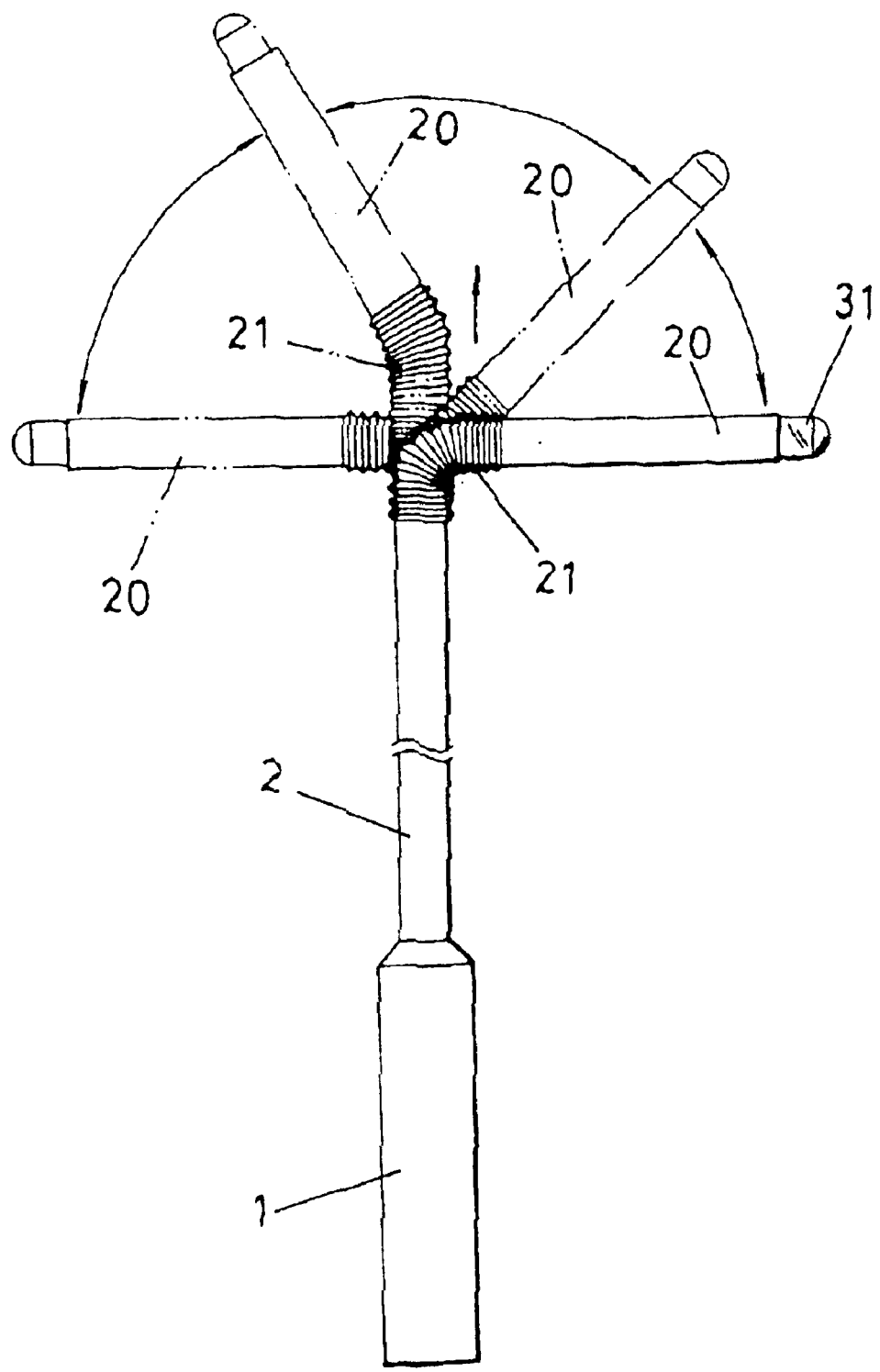
FIG. 3 shows one application of the present invention.
Figure 4:
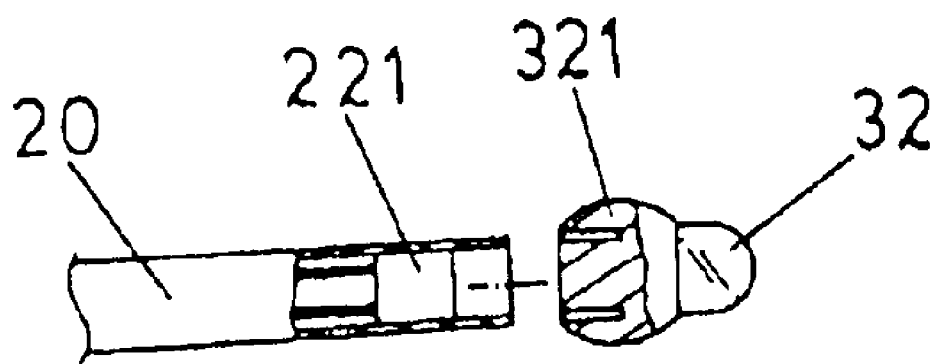
FIG. 4 is another structural view of the present invention.

The connecting end 20 of the post 2 is installed with a retaining seat 22. One end of the retaining seat 22 is connected to the conductive wire 11 and another end thereof is connected to and fixes light emitting diode (LED) 31, as shown in the FIGS. 1 and 2.

By above components, the pleated bellows portion 21 of the present invention is bendable so as to meet the confinement and requirement of the users.

Moreover, the connecting end 20 of the pleated bellows flashlight of the present invention can be connected to a bulb 32. The connecting end is installed with a retaining seat 221. A connecting seat 321 is formed with a configuration corresponding to that of the retaining seat 221. The connecting seat 321 can be combined with the bulb 32. After the connecting seat 321 is assembled to the retaining seat 221. The power can be transferred to the bulb 32.

Although the present invention has been described with reference to the preferred embodiments, it will be understood that the invention is not limited to the details described thereof. Various substitutions and modifications have been suggested in the foregoing description, and others will occur to those of ordinary skill in the art. Therefore, all such substitutions and modifications are intended to be embraced within the scope of the invention as defined in the appended claims.

What is claimed is:

1. A pleated bellows universal flashlight comprising a handle, a post and light emitting elements; characterized in that:

a battery and a power switch is installed in the handle; an upper side of the handle is extended with the post; an interior of the post is installed with a conductive wire; the conductive wire has a section for extending the length of the conductive wire; a middle section of the post is installed with a pleated bellows portion; and a connecting end of the post is installed with a retaining seat; one end of the retaining seat is connected to the conductive wire and another end thereof is connected to and fixes light emitting elements;

the pleated bellows portion is a bendable snake shape tube; and a connecting seat is formed with a configuration corresponding to that of the retaining seat; the connecting seat is combined with a bulb; after the connecting seat is assembled to the retaining seat; the power is transferred to the bulb.

2. The pleated bellows universal flashlight as claim in claim 1, wherein the light emitting element is light emitting diodes.

* * * * *